United States Patent
Uang et al.

(10) Patent No.: US 8,991,271 B2
(45) Date of Patent: Mar. 31, 2015

(54) PORTABLE NANOPARTICLE SAMPLER

(75) Inventors: Shi-nian Uang, Taipei (TW);
Chuen-Jinn Tsai, Hsinchu (TW);
Chun-Nan Liu, Taipei (TW);
Shao-Ming Hung, Kaoshiung (TW)

(73) Assignee: Institute of Occupational Safety and Health, New Taipei (TW)

( * ) Notice: Subject to any disclaimer, the term of this patent is extended or adjusted under 35 U.S.C. 154(b) by 321 days.

(21) Appl. No.: 13/599,521

(22) Filed: Aug. 30, 2012

(65) Prior Publication Data

US 2014/0060213 A1   Mar. 6, 2014

(51) Int. Cl.
*G01N 1/22* (2006.01)
*G01N 15/06* (2006.01)
*B82Y 35/00* (2011.01)
*G01N 15/00* (2006.01)

(52) U.S. Cl.
CPC ............... *G01N 1/2202* (2013.01); *B82Y 35/00* (2013.01); *G01N 1/2211* (2013.01); *G01N 15/0606* (2013.01); *G01N 2015/0038* (2013.01)
USPC ..................................................... 73/863.22

(58) Field of Classification Search
CPC . G01N 1/2202; G01N 1/2205; G01N 1/2208; G01N 1/2211
See application file for complete search history.

(56) References Cited

U.S. PATENT DOCUMENTS

| | | | | |
|---|---|---|---|---|
| 4,133,202 A | * | 1/1979 | Marple | ................... 73/28.06 |
| 4,764,186 A | * | 8/1988 | Langer | ...................... 95/268 |
| 6,270,545 B1 | * | 8/2001 | Lee et al. | ................... 55/345 |
| 8,689,648 B1 | * | 4/2014 | Heff | ..................... 73/863.22 |
| 2008/0047372 A1 | * | 2/2008 | Bridge et al. | ............ 73/863.22 |
| 2009/0272202 A1 | | 11/2009 | Uang et al. | |
| 2010/0242633 A1 | * | 9/2010 | McDevitt et al. | ......... 73/863.22 |

* cited by examiner

*Primary Examiner* — Paul West
(74) *Attorney, Agent, or Firm* — Muncy, Geissler, Olds & Lowe, P.C.

(57) ABSTRACT

A portable nanoparticle sampler for collecting respirable particulate matters and nanoparticles is composed of a tangential flow cyclone, a multi-microorifice impactor and a filter cassette. The tangential flow cyclone can remove the microparticles with cutoff aerodynamic diameter (dpa) larger than 4 µm and guide the airflow to the multi-microorifice impactor located below the cyclone. The multi-microorifice impactor includes a multi-orifice nozzle and a rotary impaction plate for enabling the microparticles with dpa from 100 nm to 4 µm to be uniformly collected on a silicone-oil-coated impaction substrate. The remnant microparticles with dpa smaller than 100 nm are collected by the filter cassette. Therefore, compared with the prior art, the portable nanoparticle sampler is characterized by low pressure loss and accurate microparticle sizing to meet the requirement of nanoparticle sampling at workplaces.

7 Claims, 4 Drawing Sheets

PORTABLE NANOPARTICLE SAMPLER

BACKGROUND OF THE INVENTION

1. Field of the Invention

The present invention relates generally to a microparticle sampler and more particularly, to a portable nanoparticle (NP) sampler.

2. Description of the Related Art

According to many studies, inhaled NPs pose a high adverse effect on human health. To assess the occupational health risk due to the exposure to the NPs in workplaces, it is necessary to collect the NPs of various diameters for further analysis of their ingredients.

A variety of NP samplers have been commercially available, including electric low-pressure impactor (ELPI), low-pressure impactor (LPI), microorifice uniform deposition impactor (MOUDI), and nano micro-orifice uniform deposition impactor (Nano-MOUDI). However, such samplers are too large and too heavy. Besides, the flow rate and the pressure loss are too high in the process of sampling to make the samplers work with small portable pumps. Thus, they could only be put at a fixed location for collecting NPs.

To measure the particle concentration at the actual workplaces more accurately, the inventors of the present invention successfully developed a personal NP sampler as disclosed in U.S. Pat. Laid-open No. 2009/0272202. The personal NP sampler is composed of a per-classifier, a nozzle, a particle-sizing filter pack, and a final filter pack from bottom to top for guiding an airflow from bottom to top to enable the airflow to be filtered by a particle-sizing filter and the final filter. Although such personal NP sampler can collect the NPs of different diameters via two stages and be applied to the small pump, the cutoff diameter of the particle-sizing filter is related to the flow rate of the airflow thereat and the flow rate is subject to the invariable number of the pores of the particle-sizing filter in such a way that a deviation happens between the cutoff diameter thereat and the default.

In other words, the aforesaid personal NP sampler though has had preferable portability but the cutoff diameter is subject to slight inaccuracy, so it still needs further improvement.

SUMMARY OF THE INVENTION

The primary objective of the present invention is to provide an NP sampler, which is portable and precise at the same time.

The foregoing objective of the present invention is attained by the NP sampler composed of a tangential flow cyclone, a multi-microorifice impactor located below the tangential flow cyclone, and a filter cassette located below the multi-microorifice impactor.

The tangential flow cyclone includes a cyclone body and an outflow duct. The cyclone body is formed of an annular portion, a top plate, and a bottom plate. The top plate and the bottom plate are mounted to a top side and a bottom side of the annular portion, respectively. A first chamber is defined between the annular portion, the top plate, and the bottom plate. An inlet is formed on the annular portion for communication with the first chamber. The outflow duct runs through the bottom plate and is provided with an entrance and an exit. The entrance is located inside the first chamber and higher than the inlet in elevation. The outflow duct allows a gas entering the first chamber to downwardly pass through the entrance and the exit and then to exit the tangential flow cyclone.

The multi-microorifice impactor includes an impaction body, a nozzle base, and an impaction plate. The impaction body defines a second chamber. The nozzle base has multiple microorifice nozzles communicating with the exit and the second chamber. The impaction plate is located inside the second chamber and right beneath the nozzle base.

The filter cassette defines a third chamber and includes a guide passage, an outlet, and a filter. The filter is mounted inside the third chamber and partitions the third chamber into a filtration chamber and an outtake chamber. The guide passage communicates with the second chamber and the filtration chamber. The outlet communicates with the outtake chamber.

The output airflow exiting the tangential flow cyclone through the exit is downward and the multi-microorifice impactor is employed, so the NP sampler of the present invention has lower pressure loss for working with a small pump. Besides, the cutoff diameter of the respirable particulate mass (RPM) collected by the multi-microorifice impactor at the second stage can be precisely maintained to the default without any deviation to help further analysis and comparison to reach the aforesaid objective of the present invention.

DETAILED DESCRIPTION OF PREFERRED EMBODIMENTS

Figure 1:
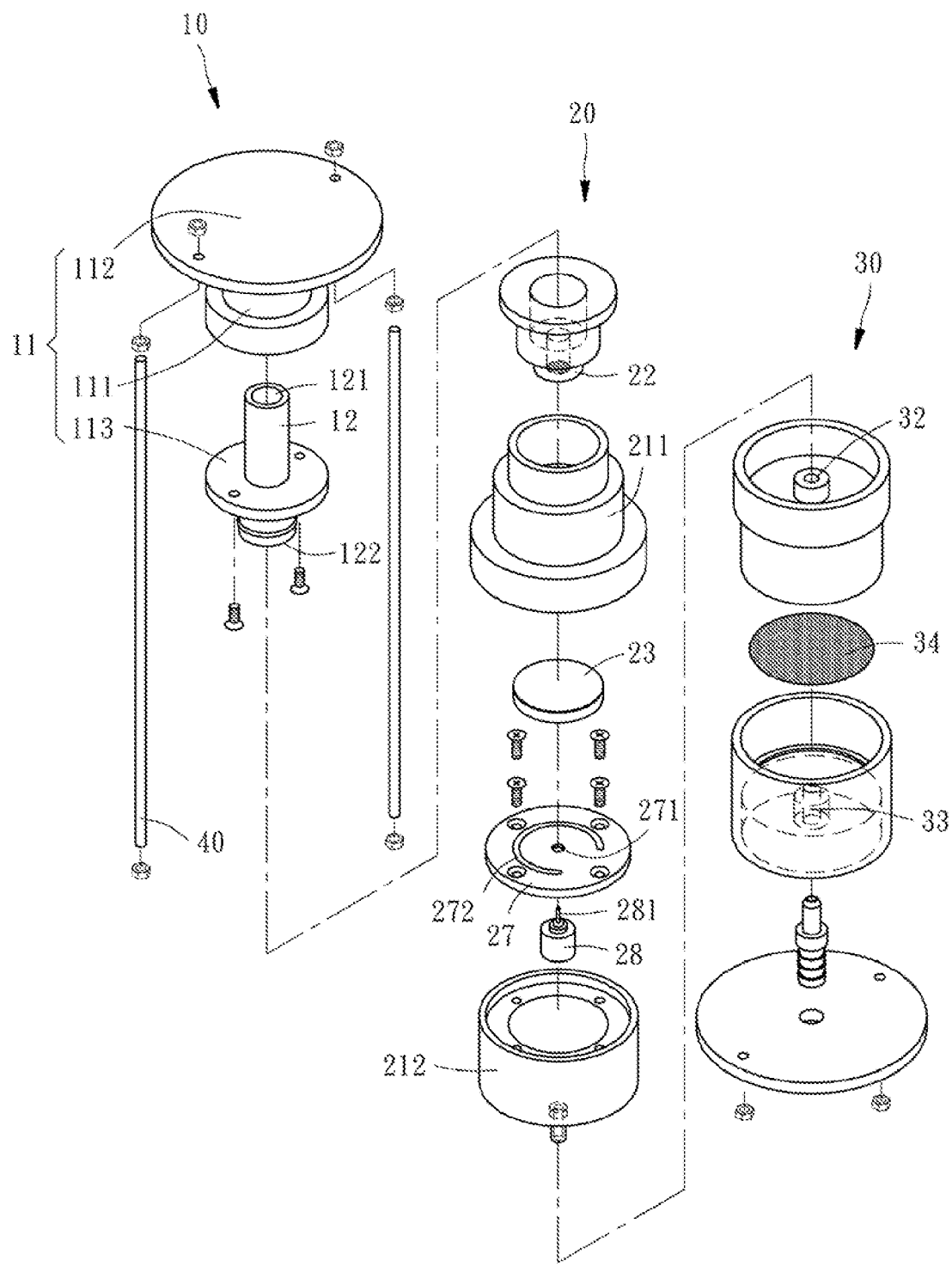
FIG. 1 is an exploded view of a preferred embodiment of the present invention.
Figure 2:
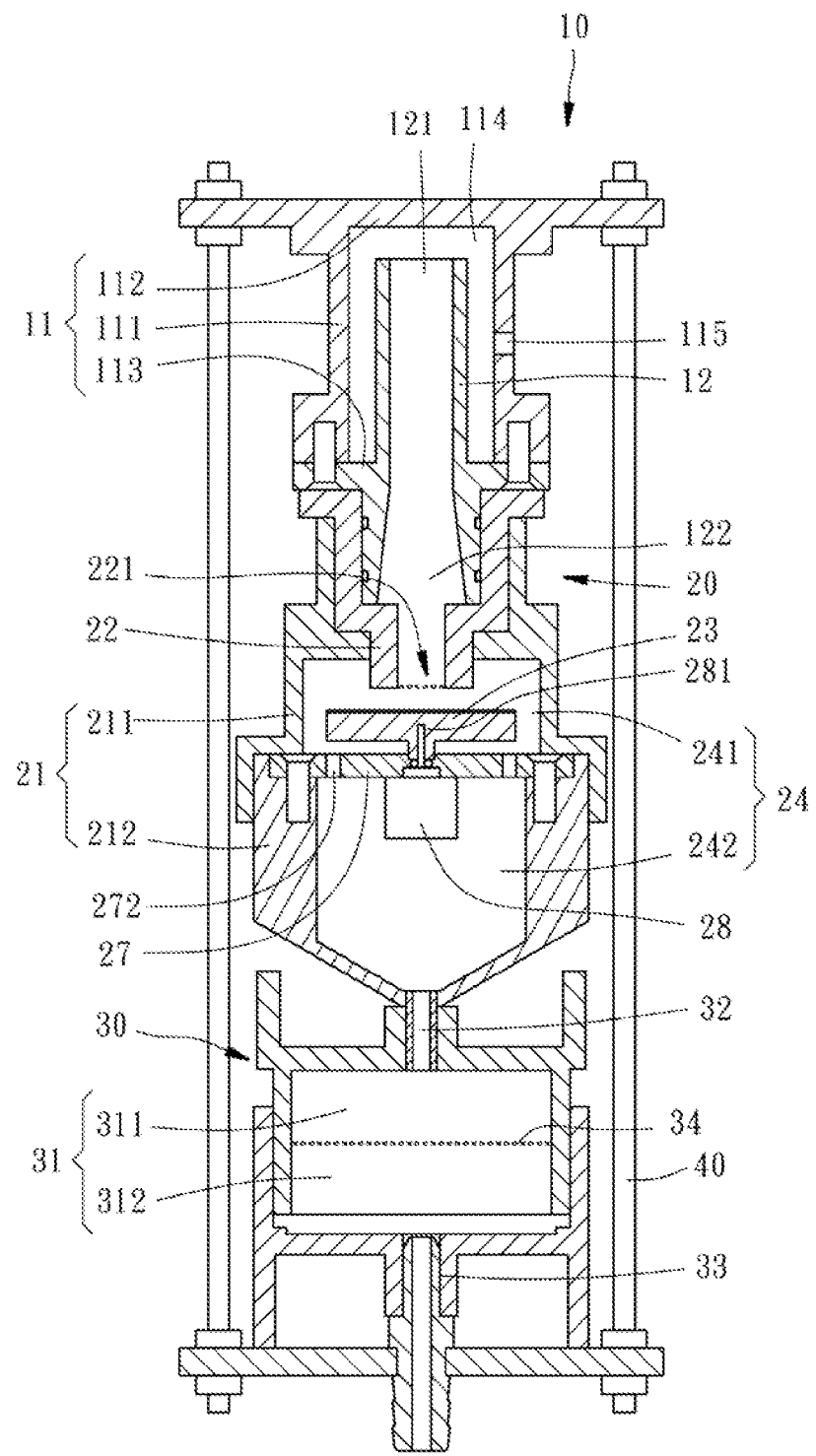
FIG. 2 is a sectional view of the preferred embodiment of the present invention.

Referring to FIGS. 1-2, a portable NP sampler constructed according to a preferred embodiment of the present invention is composed of a tangential flow cyclone 10, a multi-microorifice impactor 20 located below the tangential flow cyclone 10, and a filter cassette 30 located below the multi-microorifice impactor 20. The detailed descriptions and operations of these elements as well as their interrelation are recited in the respective paragraphs as follows. Note that the phrases "top", "bottom", "high", "lower", and "upper" are defined while the portable NP sampler is erect on the ground, i.e. according to the relative positions in gravity.

The tangential flow cyclone 10 includes a cyclone body 11 and an outflow duct 12. The cyclone body 11 has an annular portion 111, a top plate 112 mounted to a top side of the annular portion 111, and a bottom plate 113 mounted to a bottom side of the annular portion 111. A first chamber 114 is defined between the annular portion 111, the top plate 112, and the bottom plate 113. An inlet 115 is formed on the annular portion 111 for communication with the first chamber 114 and axially parallel to an imaginary tangential direction of an internal surface of the annular portion 111. The outflow duct 12 runs through the bottom plate 113 and has an entrance 121 and an exit 122. The inlet 121 is located inside the first chamber 114 and higher than the inlet 115 in elevation, so the outflow duct 12 can allow the airflow entering the first chamber 114 to downwardly exit the tangential flow cyclone 10 through the entrance 121 and the exit 122. In this embodiment, the inlet 115 has a square cross-section; on the premise that the flow rate keeps constant at 2 L/min, the diameter of the inlet 115 is 2.1 mm×2.1 mm, the cutoff diameter of the tangential flow cyclone is 4 µm.

To facilitate cleaning the first chamber 114, the bottom plate 113 can be designed to be detachably mounted to a bottom end of the annular portion 111 by threaded connection or alternative proper means. The outflow duct 12 is combined to the bottom plate 113, so when the bottom plate 113 and the annular portion 111 are separated from each other, the outflow duct 12 can be detached apart from the annular portion 111.

Figure 3:
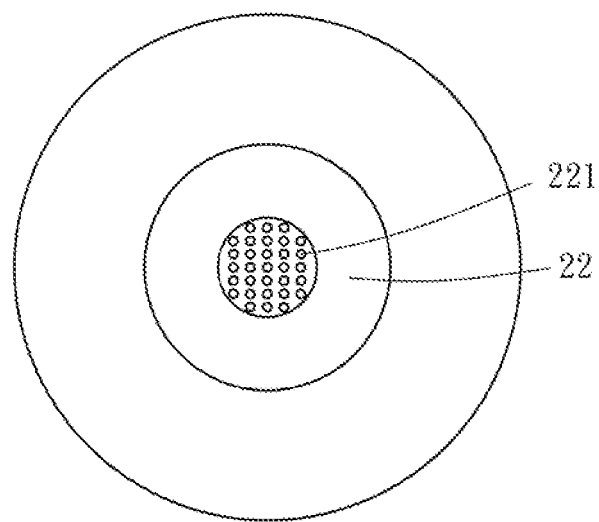
FIG. 3 is a top view of a nozzle base of the preferred embodiment of the present invention.
Figure 4:
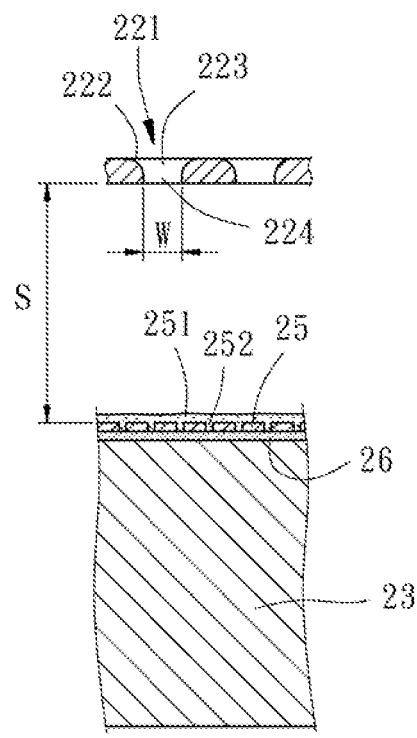
FIG. 4 is an enlarged view of a part of the preferred embodiment of the present invention, illustrating the nozzle base and the impaction plate.
Figure 5:
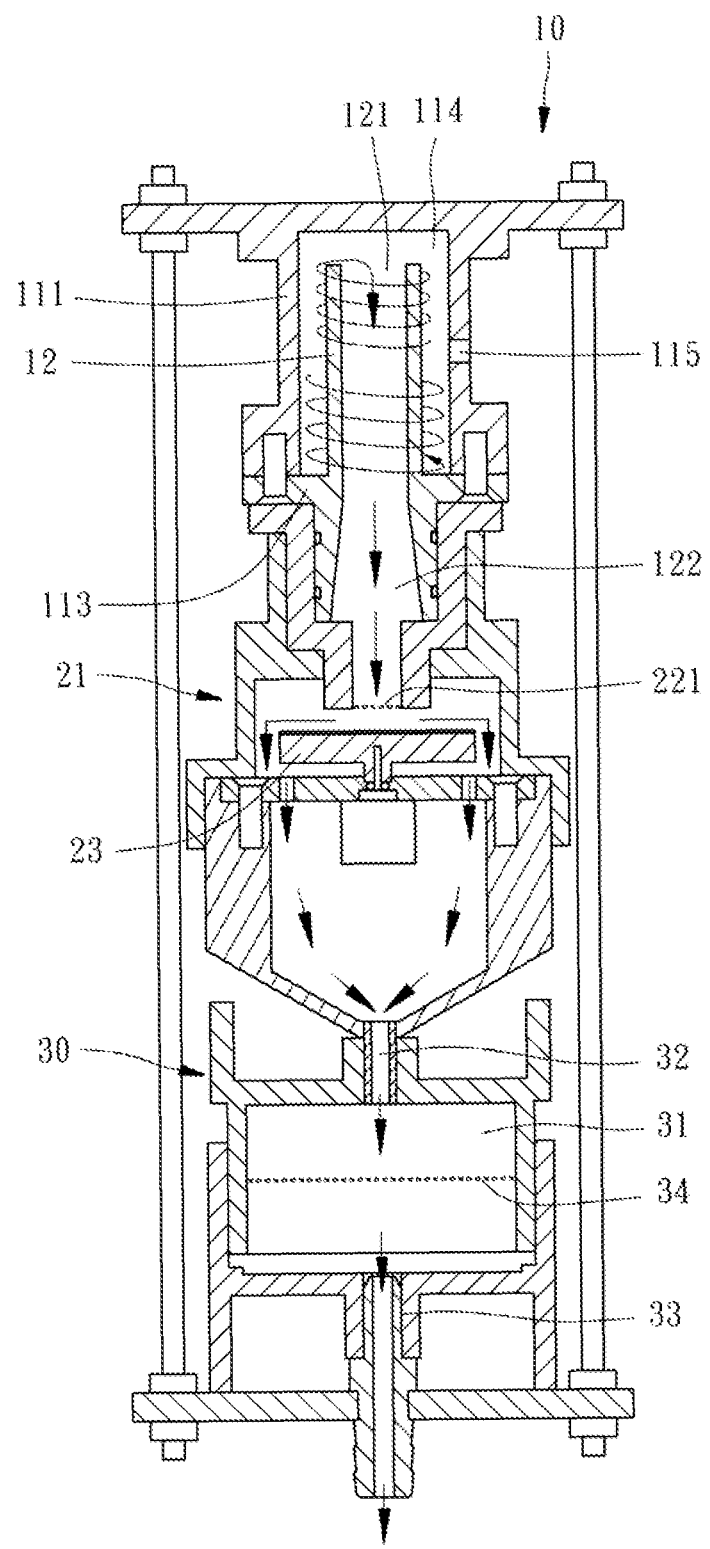
FIG. 5 is a schematic view of the preferred embodiment of the present invention at work.

The multi-microorifice impactor 20 includes an impaction body 21, a nozzle base 22, and an impaction plate 23. The impaction body 21 defines a second chamber 24 therein and is formed of an upper half part 211 and a lower half part 212. The nozzle base 22 is arranged between the impaction body 21 and the outflow duct 12. As shown in FIG. 3, the nozzle base 22 includes multiple nozzles 221 communicating with the exit 122 and the second chamber 24, respectively. The impaction plate 23 is located inside the second chamber 24 and right beneath the nozzle base 22. A predetermined gap is formed between a peripheral edge of the impaction plate 23 and a peripheral wall of the second chamber 24.

To reduce the circumstances that the nozzles 221 are jammed by microparticles, each of the nozzles 221 is provided with a smooth annular wall, a longitudinal cross-section of which is arc-shaped, and has an upper opening 223 and a lower opening 224, as shown in FIG. 4. The lower opening 224 is smaller than the upper opening 223 in diameter. To avoid or reduce particle bounce, the multi-microorifice impactor 20 further includes an impaction substrate 25 disposed on a top side of the impaction plate 23 and coated with silicone oil 251. To prevent the silicone oil 251 from dispersion resulting from air jet and to further avoid particle bounce, the impaction substrate 25 can preferably be a Teflon filter with a pore size of 10 μm, having a plurality of pores 252 for preventing dispersion of the silicone oil and effectively avoiding particle bounce. Alternatively, the impaction substrate 25 can be excluded from the present invention. Besides, to facilitate weighing after sampling, an aluminum foil 26 or a thin support piece made of other material can be mounted between the impaction substrate 25 and the impaction plate 23. In this way, the aluminum foil 26, the impaction substrate 25, and the silicone oil 251 can be weighed as well as collected microparticles after the sampling.

Let reference character W denote the diameter of the lower opening 224 of each nozzle 221. Let reference character S denote the distance between the lower opening 224 and the top side of the impaction plate 23 because the surface of the impaction substrate 25 is regarded as the extension of the top side of the impaction plate 23 and the silicone oil 251 is subject to dispersion resulting from the air jet to be appressed onto the surface of the impaction substrate 25. The number of the nozzles 221 is 137 as an example. When the specific value (S/W) is 13.8, the cutoff diameter of the multi-microorifice impactor 20 is about 100 nm, i.e. the microparticles with diameters of 100 nm to 4 μm will be collected by the multi-microorifice impactor 20. The cutoff diameter of the multi-microorifice impactor 20 can be precisely controlled by change of the aforesaid specific value. In practice, the cutoff diameter of the multi-microorifice impactor 20 is not limited to 100 nm.

In addition, to make the distribution of the microparticles be more uniform, the multi-microorifice impactor 20 can further include a fastening plate 27 and a motor 28, both of which are located inside the second chamber 24. The fastening plate 27 partitions the second chamber 24 into an upper chamber 241 and a lower chamber 242. The fastening plate 27 includes an axial hole 271 and a U-shaped flow guide hole 272 communicating with the upper and lower chambers 241 and 242. The motor 28 includes a rotary shaft 281 rotatably inserted into the axial hole 271 and synchronically connected to the impaction plate 23. The impaction plate 23 and the motor 28 are located inside the upper and lower chambers 241 and 242, respectively. When the rotary shaft 281 of the motor 28 is rotated, the impaction plate 23 can be driven for rotation together at a predetermined 1 rpm in such a way that the microparticles can be distributed preferably uniformly on the impaction substrate 25 to effectively avoid particle bounce occurring when the microparticles are centered to particular positions.

The filter cassette 30 defines a third chamber 31 therein and includes a guide passage 32, an outlet 33, and a filter 34. The filter 34 is mounted to the third chamber 31 to partition the third chamber 31 into a filtration chamber 311 and an outtake chamber 312 for collecting the remnant microparticles indicating those with a size smaller than 10 nm in this embodiment. The guide passage 32 communicates with the lower chamber 242 and the filtration chamber 311. The outlet 33 communicates with the outtake chamber 312 and is connected with a piping communicating with a suction pump, which is portable, such as portable high-pressure-loss pump (Model No. XR5000) developed by SKC Inc., PA, USA, 8 cm (Length)×6 cm (Width)×10 cm (Height), 1054 g (Weight; battery included); its size and weight facilitate a user to carry it with himself or herself. Besides, to increase the flow rate of the airflow from the second chamber 24 to the third chamber 31, the second chamber 24 can have a taper-shaped bottom side. However, the bottom side of the second chamber 24 is not limited to taper in shape.

Furthermore, the NP sampler of the present invention can further include a plurality of fastening bars 40 for forcing the tangential flow cyclone 10 and the filter cassette 30 to approach toward the multi-microorifice impactor 20 for fixation.

Referring to FIG. 5, in operation, when a suction pump is used for pumping the air, the airflow enters the first chamber 114 through the inlet 115 of the tangential flow cyclone 10 and firstly flows spirally downwardly along the internal wall of the annular portion 111 subject to the gravity and inertial action to enable the microparticles of larger diameters to be thrown to the internal wall of the annular portion 111 and then sunk on the bottom plate 113. When flowing to the bottom plate 113, the airflow can flow spirally upwardly along an external wall of the outflow duct 12 and finally exit the tangential flow cyclone 10 through the entrance 121 and exit 122 by order. In this embodiment, the cutoff diameter of the tangential flow cyclone 10 is about 4 μm.

The airflow continues to pass through the nozzles 221, flow along the gap between the impaction plate 23 and the impaction body 21, and then veer, meanwhile, the larger microparticles impinge on the impaction plate 23 due to inertia to be collected by the impaction substrate 25 and the silicone oil 251 thereon. In this embodiment, the cutoff diameter of the multi-microorifice impactor 20 is 100 nm.

At last, the airflow enters the third chamber 31 through the guide passage 32, such that the microparticles with diameters smaller than 100 nm will be collected by the filter 34 and the clean airflow continue to exit the filter cassette 30 through the outlet 33.

After a predetermined time, stop the sampling and take out the impaction substrate 25 along with the aluminum foil 26 and the silicone oil 251 to weigh them, and then calculate the total weight of the RPMs with diameters of 4 μm to 100 nm; next, take out the filter 34 to weigh it and then calculate the total weight of the NPs with diameters smaller than 100 nm. In this way, exposure of workers to RPMs and NPs at the sampling place can be accessed.

In light of the special design of the aforesaid embodiment, the NP sampler of the present invention is not only structurally compact and portable but the tangential flow cyclone, the multi-microorifice impactor, and the filter cassette have highly precise cutoff diameters, respectively.

In particular, the evident difference between the tangential flow cyclone of the present invention and the conventional tangential flow cyclone lies in direction of output airflow. To effectively separate the microparticles from the airflow, the airflow in each of the conventional tangential flow cyclones disclosed on the textbooks or in practice is upward in direction as disclosed, for example, in aforesaid U.S. Pat. Laid-open No. 2009/0272202. For a long time, the upward output airflow of the tangential flow cyclone has become a technical prejudice in the art and is contrary to the input airflow required by the multi-microorifice impactor that should be downward in direction. Owing to such characteristic of congenital incompatibility, none of any nanoparticle sampler composed of the tangential flow cyclone and the multi-microrifice impactor had been available. However, the inventors of the present invention become aware that if the direction of output airflow of the tangential flow cyclone is properly changed, it will not only reach the effect of separating the microparticles but be combined with the multi-microorifice impactor to become a low-pressure-drop two-stage microparticle separator, which is very applicable to the portable nanoparticle samplers stressing on portability. In this way, the precise and convenient microparticle sampling operation can be fulfilled.

What are disclosed above is the preferred embodiment of the present invention only and the person skilled in the art can simply interchange or modify the structure, e.g. modifying the cutoff diameter of each component or respective components are connected by other means; modifying the U-shaped flow guide hole of the fastening plate to other shape; or further dividing it into a plurality of guide holes for communication with the upper and lower chamber.

Although the present invention has been described with respect to a specific preferred embodiment thereof, it is in no way limited to the specifics of the illustrated structures but changes and modifications may be made within the scope of the appended claims.

What is claimed is:

1. A portable nanoparticle sampler comprising:
a tangential flow cyclone having a cyclone body and an outflow duct, the cyclone body having an annular portion, a top plate, and a bottom plate, the top plate being mounted to a top side of the annular portion, the bottom plate being mounted to a bottom side of the annular portion, a first chamber being defined between the annular portion, the top plate, and the bottom plate, an inlet being formed on the annular portion for communication with the first chamber, the outflow duct running through the bottom plate and having an entrance and an exit, the entrance being located inside the first chamber and higher than the inlet in elevation, the outflow duct being adapted to enable the airflow entering the first chamber to downwardly exit the tangential flow cyclone through the entrance and the exit by order;
a multi-microorifice impactor located below the tangential flow cyclone and having an impaction body, a nozzle base, and an impaction plate, the impaction body defining a second chamber therein, the nozzle base having a plurality of nozzles communicating with the exit and the second chamber, the impaction plate being located inside the second chamber and right below the nozzle base; and
a filter cassette located below the multi-microorifice impactor, the filter cassette defining a third chamber therein and having a guide passage, an outlet, and a filter, the filter being mounted inside the third chamber and partitioning the third chamber into a filtration chamber and an outtake chamber, the guide passage communicating with the second chamber and the filtration chamber, the outlet communicating with the outtake chamber,
wherein the bottom plate of the cyclone body is detachably mounted to a bottom end of the annular portion.

2. The portable nanoparticle sampler as defined in claim 1, wherein the second chamber comprises a taper-shaped bottom side.

3. The portable nanoparticle sampler as defined in claim 1, wherein the multi-microorifice impactor further comprises an impaction substrate disposed on a top side of the impaction plate, the impaction substrate being coated with silicone oil.

4. The portable nanoparticle sampler as defined in claim 1, wherein each of the nozzles is defined by a smooth annular wall to have an upper opening and a lower opening, the lower opening being smaller than the upper opening in diameter.

5. A portable nanoparticle sampler comprising:
a tangential flow cyclone having a cyclone body and an outflow duct, the cyclone body having an annular portion, a top plate, and a bottom plate, the top plate being mounted to a top side of the annular portion, the bottom plate being mounted to a bottom side of the annular portion, a first chamber being defined between the annular portion, the top plate, and the bottom plate, an inlet being formed on the annular portion for communication with the first chamber, the outflow duct running through the bottom plate and having an entrance and an exit, the entrance being located inside the first chamber and higher than the inlet in elevation, the outflow duct being adapted to enable the airflow entering the first chamber to downwardly exit the tangential flow cyclone through the entrance and the exit by order;
a multi-microorifice impactor located below the tangential flow cyclone and having an impaction body, a nozzle base, and an impaction plate, the impaction body defining a second chamber therein, the nozzle base having a plurality of nozzles communicating with the exit and the second chamber, the impaction plate being located inside the second chamber and right below the nozzle base; and
a filter cassette located below the multi-microorifice impactor, the filter cassette defining a third chamber therein and having a guide passage, an outlet, and a filter, the filter being mounted inside the third chamber and partitioning the third chamber into a filtration chamber and an outtake chamber, the guide passage communicating with the second chamber and the filtration chamber, the outlet communicating with the outtake chamber,
wherein the multi-microorifice impactor further comprises a fastening plate and a motor, both of which are located inside the second chamber, the fastening plate partitioning the second chamber into an upper chamber and a lower chamber and having an axial hole and at least one guide hole communicating with the upper and lower chambers, the motor having a rotary shaft rotatably inserted into the axial hole and synchronically connected with the impaction plate; the impaction plate and the motor are located inside the upper and lower chambers, respectively.

6. A portable nanoparticle sampler comprising:
a tangential flow cyclone having a cyclone body and an outflow duct, the cyclone body having an annular portion, a top plate, and a bottom plate, the top plate being mounted to a top side of the annular portion, the bottom plate being mounted to a bottom side of the annular portion, a first chamber being defined between the annular portion, the top plate, and the bottom plate, an inlet being formed on the annular portion for communication with the first chamber, the outflow duct running through the bottom plate and having an entrance and an exit, the entrance being located inside the first chamber and higher than the inlet in elevation, the outflow duct being adapted to enable the airflow entering the first chamber to downwardly exit the tangential flow cyclone through the entrance and the exit by order;

a multi-microorifice impactor located below the tangential flow cyclone and having an impaction body, a nozzle base, and an impaction plate, the impaction body defining a second chamber therein, the nozzle base having a plurality of nozzles communicating with the exit and the second chamber, the impaction plate being located inside the second chamber and right below the nozzle base; and a filter cassette located below the multi-microorifice impactor, the filter cassette defining a third chamber therein and having a guide passage, an outlet, and a filter, the filter being mounted inside the third chamber and partitioning the third chamber into a filtration chamber and an outtake chamber, the guide passage communicating with the second chamber and the filtration chamber, the outlet communicating with the outtake chamber, wherein the multi-microorifice impactor further comprises an impaction substrate disposed on a top side of the impaction plate, the impaction substrate being coated with silicone oil, and wherein the multi-microorifice impactor further comprises an aluminum foil mounted between the impaction substrate and the impaction plate.

7. The portable nanoparticle sampler as defined in claim 6, wherein the impaction substrate is a polytetrafluoroethene filter.

* * * * *